United States Patent [19]

Miles

[11] Patent Number: 5,631,943
[45] Date of Patent: May 20, 1997

[54] PORTABLE X-RAY DEVICE

[76] Inventor: Dale A. Miles, 13201 Brookshire Pkwy., Carmel, Ind. 46033

[21] Appl. No.: 574,768

[22] Filed: Dec. 19, 1995

Related U.S. Application Data

[60] Provisional application No. 60/004,988, Nov. 10, 1995.

[51] Int. Cl.$^6$ ............................... H05G 1/10; H05G 1/56
[52] U.S. Cl. ............................. 378/102; 378/117; 378/147
[58] Field of Search ................................ 378/102, 117, 378/198, 114, 147

[56] References Cited

U.S. PATENT DOCUMENTS

| | | | |
|---|---|---|---|
| 4,117,334 | 9/1978 | Strauts | 250/402 |
| 4,384,360 | 5/1983 | Kitadate et al. | 378/202 |
| 4,646,338 | 2/1987 | Skillicorn | 378/110 |
| 4,720,844 | 1/1988 | Bougle | 378/101 |
| 4,856,036 | 8/1989 | Malcolm et al. | 378/116 |
| 4,924,485 | 5/1990 | Hoeberling | 378/102 |
| 4,975,937 | 12/1990 | Horton et al. | 378/114 |

OTHER PUBLICATIONS

"Radiographic Cones and Immobilizers Superficial Therapy Cones and Specula" General Electric X–Ray Corporation, 1941.

*Primary Examiner*—David P. Porta
*Assistant Examiner*—David Vernon Bruce
*Attorney, Agent, or Firm*—Woodard, Emhardt, Naughton, Moriarty & McNett

[57] ABSTRACT

A portable and preferably hand-held X-ray generator for use in intraoral and other X-ray applications, and a new process of dental image acquisition which utilizes a novel receptor holder physically linked to the lightweight, portable generator, and a unique, articulating arm and cradle which allows one generator to be used in multiple operatories. The system's generator has a reduced X-ray output and much smaller focal spot area than conventional dental X-ray generators, which reduces the X-ray output and the overall patient X-ray burden. The smaller focal spot also allows for improved resolution in the final image.

17 Claims, 8 Drawing Sheets

PORTABLE X-RAY DEVICE

CROSS REFERENCE TO RELATED APPLICATIONS

The present application is related to provisional patent application Ser. No. 60/004,988, filed Oct. 10, 1995 by Melvin P. Sledband and entitled HAND X-RAY UNIT WITH SMALL GENERATOR, TUBE AND TUBEHEAD, which application is incorporated by reference herein in its entirety.

TECHNICAL FIELD OF THE INVENTION

The present invention relates generally to X-ray devices and, more particularly, to portable X-ray devices.

BACKGROUND OF THE INVENTION

For decades, medical professionals, such as dentists, have routinely used X-ray radiographs for disease detection, diagnostic decision making and treatment monitoring. X-rays are emitted by an X-ray generator, pass through the structures of interest such as teeth, bone and soft tissues of the head and jaws, and are captured by an appropriate receptor. The traditional receptor, X-ray photographic film, is still the most widely used. In such film-based systems, the latent image is produced on the film through activation of silver halide crystals which are then rendered visible by processing the exposed film in chemical solutions. Such film processing takes several minutes when a series of X-ray films are exposed on the patient. If, after developing, the images are discovered to be unusable due to film placement or image geometry errors, a new series of films need to be exposed. This increases the patient x-ray dose.

Recently, systems have been introduced for electronic acquisition of dental X-ray information through the use of charge coupled device (CCD) image receptors. Current CCD receptors for oral, intraoral and maxillofacial imaging tasks use either radiation-hardened CCD arrays (Regain SensAray, Sundvaal, Sweden) or CCD arrays coupled to a scintillator such as a rare-earth X-ray screen material (Trophy Radiologie, Vincennes, France). The largest area array currently used in dental imaging is now approximately 760 pixels by 524 pixels (Schick Technologies, New York), which results in a resolution of about 10 line pairs/mm.

Imaging with a CCD receptor requires approximately 70–80% less exposure time than imaging with X-ray film. Thus, the patient X-ray dose is lessened. However, most current X-ray generators were designed for use with film receptors; consequently, they produce too much X-ray radiation, overloading the CCD receptor and increasing the patient absorbed X-ray dose.

Another problem with current X-ray generators is that they are large and heavy, thereby requiring that they be installed in a fixed location. For dental applications, the X-ray generator is typically fixedly mounted to the distal end of an articulating arm which is in turn mounted to the wall of the dental operatory. The weight of the tubehead often requires the placement of additional support in the wall where the unit is mounted in order to support the tubehead at its maximum length from the wall. Because a dental office normally includes several operatories, the provision of X-ray imaging capability to each of the operatories requires a substantial investment since multiple X-ray units must be purchased.

There is, therefore, a need for an X-ray device that will lessen the patient X-ray dose. There is also a need for an X-ray device that can easily be used in several different operatories in order to reduce duplication of equipment within the dental office. The present invention is directed toward meeting these needs.

SUMMARY OF THE INVENTION

The present invention relates to a portable and preferably hand-held X-ray generator for use in intraoral and other X-ray applications, and a new process of dental image acquisition which utilizes a novel receptor holder physically linked to the lightweight, portable generator, and a unique, articulating arm and cradle which allows one generator to be used in multiple operatories. The system's generator has a reduced X-ray output and much smaller focal spot area than conventional dental X-ray generators, which reduces the X-ray output and the overall patient X-ray burden. The smaller focal spot also allows for improved resolution in the final image.

In one form of the invention, a portable X-ray device is disclosed, comprising a handle configured to be held by a single hand; an X-ray tube mounted within the handle; a collimated tube mounted to the handle and positioned such that X-rays will be emitted into the collimated tube when the X-ray tube is activated; wiring extending between an interior of the handle and an exterior of the handle and operative to couple an external power supply to the X-ray tube; an enable switch mounted to the handle; and an exposure switch mounted to the handle; wherein the X-ray tube will only emit X-rays when the enable switch and the exposure switch are both depressed.

In another form of the invention, a portable X-ray device is disclosed, comprising an enclosure; an X-ray tube mounted within the enclosure; a collimated tube mounted to the handle and positioned such that X-rays will be emitted into the collimated tube when the X-ray tube is activated; wiring extending between an interior of the enclosure and an exterior of the enclosure and operative to couple an external power supply to the X-ray tube; and power supply circuitry operative to generate a voltage to drive the X-ray tube, wherein the power supply circuitry is not contained within the enclosure and is coupled to the enclosure by the wiring; whereby a weight of the enclosure is significantly reduced.

In another form of the invention, an X-ray image receptor holder adapted to be coupled to a source of X-rays is disclosed, the holder comprising an image receptor holder coupled to the collimated tube, the holder comprising: a horizontal member having proximal and distal ends; a vertical member attached to the horizontal member distal end and extending transversely thereto; and a transverse sliding member mounted to the horizontal member and operative to slide thereon in a longitudinal direction; wherein an X-ray image receptor may be held between the vertical member and the sliding member.

In another form of the invention, a method for generating an X-ray image is disclosed, comprising the steps of: (a) providing a portable X-ray device, comprising: a handle configured to be held by a single hand; an X-ray tube mounted within the handle; a collimated tube mounted to the handle and positioned such that X-rays will be emitted into the collimated tube when the X-ray tube is activated; wiring extending between an interior of the handle and an exterior of the handle and operative to couple an external power supply to the X-ray tube; an enable switch mounted to the handle; and an exposure switch mounted to the handle; wherein the X-ray tube will only emit X-rays when the enable switch and the exposure switch are both depressed;

(b) grasping the handle with a single hand; (c) depressing the enable switch with a first finger of the hand; (d) aiming the collimated tube at an X-ray image receptor, wherein a structure to be imaged is positioned between the collimated tube and the receptor; and (e) depressing the exposure switch with a second finger of the hand while holding the enable switch in a depressed position.

In another form of the inventor a method for generating an X-ray image is disclosed, comprising the step of: (a) providing a portable X-ray device, comprising: an enclosure; an X-ray tube mounted within the enclosure; a collimated tube mounted to the handle and positioned such that X-rays will be emitted into the collimated tube when the X-ray tube is activated; wiring extending between an interior of the enclosure and an exterior of the enclosure and operative to couple an external power supply to the X-ray tube; and power supply circuitry operative to generate a voltage to drive the X-ray tube, wherein the power supply circuitry is not contained within the enclosure and is coupled to the enclosure by the wiring; whereby a weight of the enclosure is significantly reduced; (b) providing an articulating arm having a cradle thereon, wherein the cradle is adapted to hold the X-ray device when placed therein; (c) aiming the collimated tube at an X-ray image receptor, wherein a structure to be imaged is positioned between the collimated tube and the receptor; (d) moving the articulated arm such that the cradle will hold the X-ray device; (e) depressing an enable switch; and (f) depressing an exposure switch, wherein the X-ray device will not emit X-rays unless both the enable switch and the exposure switch are depressed.

DETAILED DESCRIPTION OF THE PREFERRED EMBODIMENTS

Figure 1:
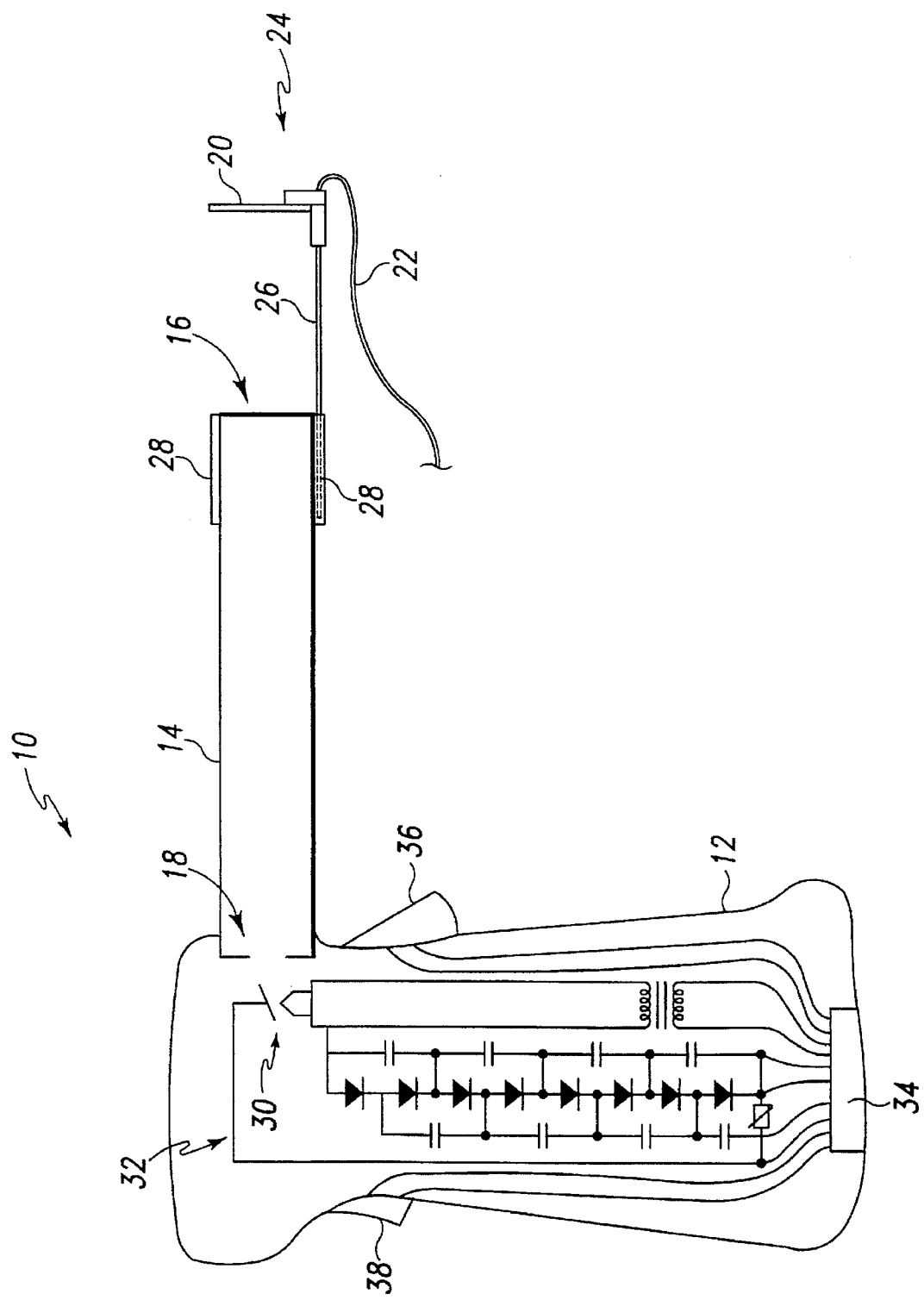
FIG. 1 is a schematic side cross-sectional view of a first embodiment portable X-ray generator of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention relates to a portable and preferably hand-held X-ray generator for use in intraoral and other X-ray applications, and a new process of dental image acquisition which utilizes a novel receptor holder physically linked to the lightweight, portable generator, and a unique, articulating arm and cradle which allows one generator to be used in multiple operatories. The system's generator has a reduced X-ray output and much smaller focal spot area than conventional dental X-ray generators, which reduces the X-ray output and the overall patient X-ray burden. The smaller focal spot also allows for improved resolution in the final image.

Referring to FIG. 1, a preferred embodiment of the portable X-ray generator of the present invention is illustrated and indicated generally at 10. The X-ray generator 10 is illustrated in cross-sectional view in FIG. 1 and includes a "pistol grip" handle 12 to which is attached a rectangular collimated tube 14. The handle 12 and tube 14 are preferably formed from LITHARCH lead ceramic material or from a lead-lined, high density plastic. The distal opening 16 of the collimated tube 14 is preferably 2.5 centimeters by 3.0 centimeters. The size of the distal opening 16 is preferably sized to be just slightly larger than the receptor size to be used with the X-ray generator 10. The proximal end of the tube 14 includes a rectangular, aluminum collimator which has an aperture (port or exit) of approximately 3 millimeters by 5 millimeters.

An X-ray receptor 20 is provided for recording the X-ray image. The X-ray receptor 20 may be any device which is sensitive to X-ray radiation, such as X-ray film or a CCD sensor. The receptor 20 is illustrated as a CCD sensor in FIG. 1, including the wiring 22 which is used to couple the CCD receptor 20 to a recording and display device as is known in the art. The CCD receptor 20 is positioned in a receptor holder 24 which is coupled to a rod 26 which is adapted to fit within any one of a plurality of docking slots 28 formed on the distal end of the collimated tube 14. The design and operation of the receptor holder 24 and docking slots 28 is discussed in greater detail hereinbelow.

The handle 12 of the X-ray generator 10 includes an X-ray tube 30 and associated driving circuitry 32. The X-ray tube 30 and driving circuitry 32 are described in greater detail hereinbelow with respect to FIG. 4. Because it is desired that the present invention comprise a portable and preferably hand-held X-ray generator, the isolation transformer normally used in X-ray generators has been eliminated in the present invention. Furthermore, the high voltage transformer is not placed within the handle 12, but is remote from the X-ray generator 10 and the high voltage signal is wired from the high voltage transformer to the circuitry 32 within the handle 12, as explained in greater detail hereinbelow. The handle 12 is filled with oil or preferably gas in order to dissipate heat generated by the X-ray tube 30, as is known in the art. The distance from the collimator 18 to the distal end 16 of the collimated tube 14 is preferably 15 centimeters.

The rectangular, collimated tube 14 is much smaller than the conventional round cone used in almost every prior art dental X-ray tubehead. The diameter of the prior art round cone is approximately 2.75", whereas the tube 14 dimensions are preferably only 2.0"×1.5". This smaller size is possible because the receptor is uniquely fixed to the generator. This arrangement leads to smaller skin surface X-ray dose and to a potential X-ray dose reduction by eliminating retakes of filing because of vertical or horizontal angulation errors which occur frequently when a free-floating conventional tubehead is aimed at the film by the operator. In addition the preferred 0.3 mm focal spot is ½ the size of the smallest focal spot presently available in the prior art devices.

The various input and output connections of the circuitry 32 are coupled to an electrical connector 34 mounted in the base of the handle 12. These connections are described in greater detail hereinbelow. Also coupled to the connector 34 are an enable switch 36 and a fire switch 38. The enable switch 36 is preferably located on the handle 12 at a position where it will be convenient to be depressed by the index finger of the user. As described in greater detail hereinbelow, the enable switch 36 initiates current flow to warm up the X-ray tube 30 prior to actual firing of the X-ray generator 10. After the enable switch 36 has been depressed, the operator depresses the fire switch 38 in order to activate the X-ray generator 10. The fire switch 38 is preferably located on the handle 12 at a position which is conveniently accessed by the operator's thumb. The two switch configuration should act as a safeguard against inadvertant firing of the unit and is described in greater detail hereinbelow. Those skilled in the art will appreciate that the wiring within the handle 12 may be hard-wired to the external circuitry rather than using the electrical connector 34.

Figure 2:
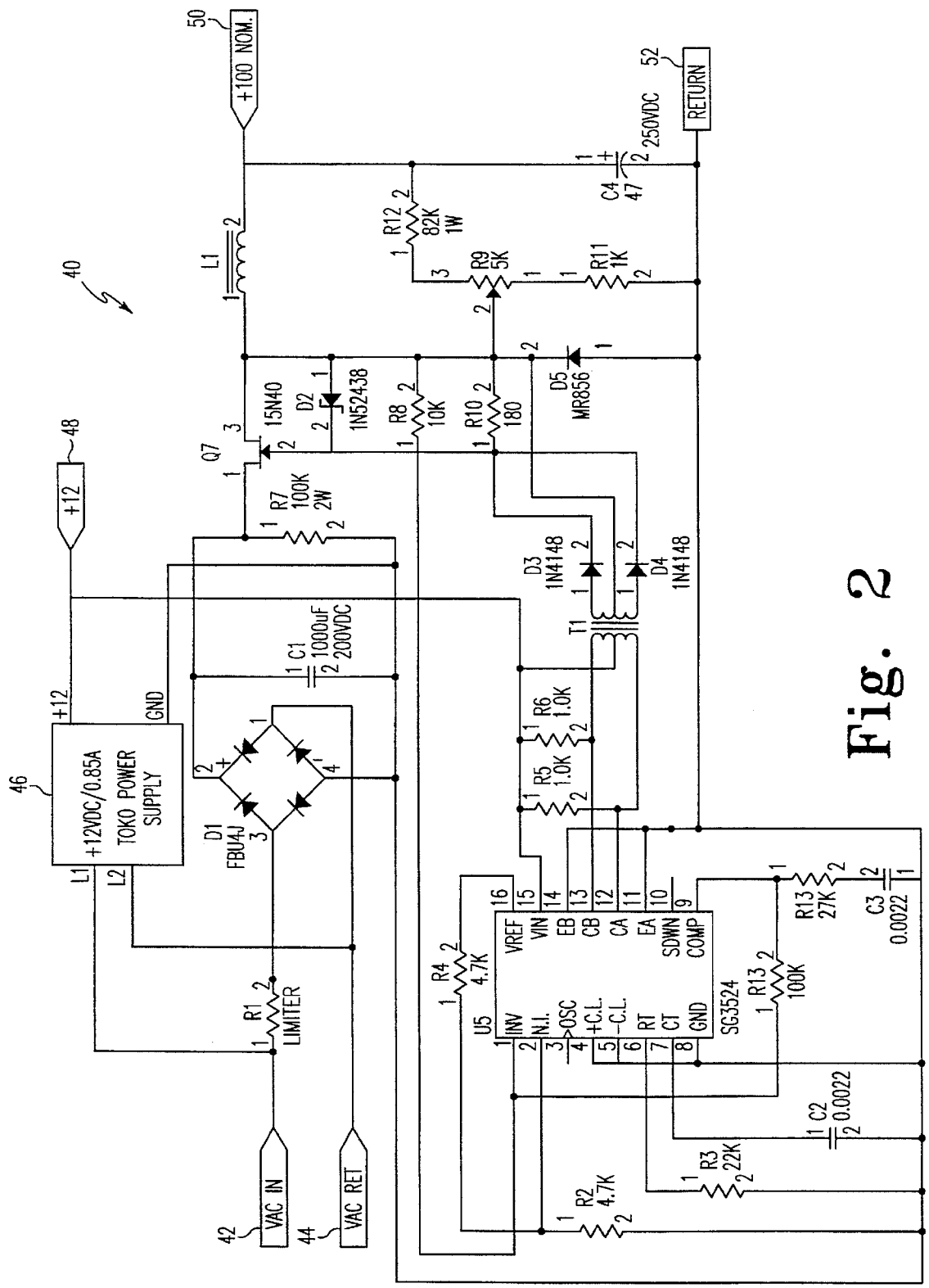
FIG. 2 is a schematic circuit diagram of a power supply circuit of the present invention.

Referring now to FIG. 2, a power supply circuit for the hand-held X-ray generator of the present invention is illustrated, and indicated generally at 40. The power supply circuit 40 is preferably not contained within the handle 12 in order to reduce the weight thereof. Instead the power supply circuit 40 is contained in a separate housing and is coupled to the handle 12 via cabling (see FIG. 10). The circuit 40 is coupled to a standard 110 volt power line at inputs 42 and 44. The 110 volt inputs 42 and 44 are coupled to a 12 volt regulator 46 in order to produce the 12 volt output 48, as is known in the art. The power line inputs 42 and 44 are further coupled to a full wave rectifier D1. The output ports of the full wave rectifier D1 are placed across the 1,000 uF capacitor C1. The voltage placed across the capacitor C1 is typically 160 volts DC. A switching regulator controller chip U5 (such as a SG3524) produces two control outputs CA and CB which are coupled to the transformer T1. The transformer T1 preferably has a 120 turn center tapped primary and an 84 turn center tapped secondary. The transformer T1 combines the two control signals into a single signal feeding a series power field effect transistor (FET) Q7.

The duty cycle of the power FET Q7 determines the output voltage presented at output ports 50 and 52. The switching regulator U5 feeds current to a series inductor L1 and that current (i) increases at a rate determined by the voltage difference (v) across the inductor L1 and the inductance (L) according to the formula:

$$v = L\,di/dt$$

After a few microseconds, the FET Q7 is switched off and the inductance L causes the input voltage of the inductor L1 to switch rapidly to ground, where it is caught by the clamp diode D5, at which point the current starts to ramp down according to the following formula:

$$v' = -L\,di/dt$$

(where v' is the output voltage appearing across the terminals 50 and 52).

The ratio of the on and off times determines the output voltage and the switching regulator U5 controls this. The switching regulator is very efficient, and generates very little heat and the parts for the power supply circuit 40 are small and inexpensive. It will be appreciated by those skilled in the art that the circuit 40 is essentially tied to the power line at the inputs 42 and 44, with only the rectifier D1 for isolation. The present invention, therefore, eliminates the isolation transformer normally used in such systems in order to keep the system small and light weight. The output voltage appearing across the terminals 50 and 52 is nominally +100 VDC, but may be set anywhere between +40 and +120 VDC in order to set the X-ray tube 30 anode voltage between 20 and 80 kVp.

Figure 3:
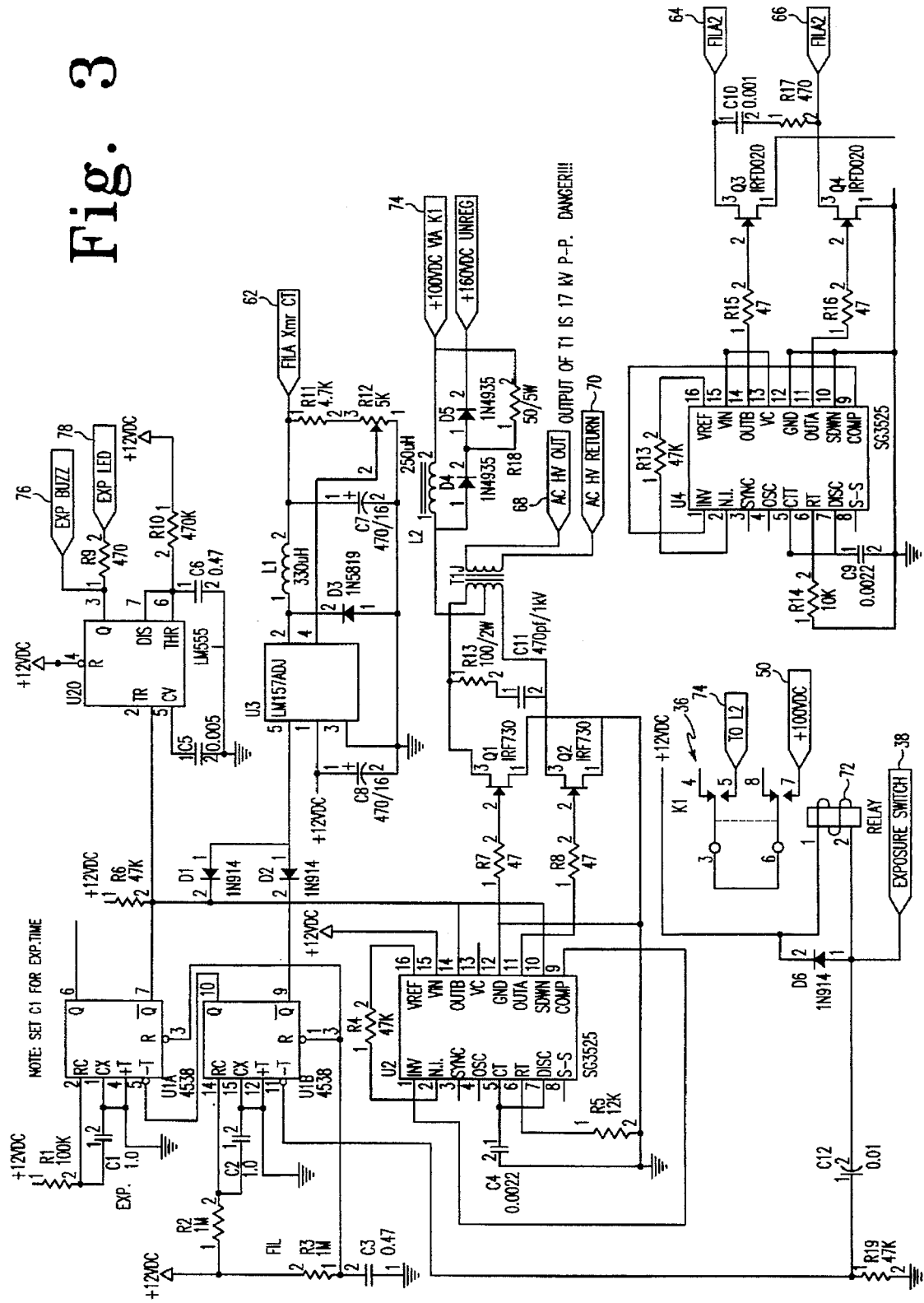
FIG. 3 is a schematic circuit diagram of a timing and control circuit of the present invention.

Referring now to FIG. 3, a control circuit of the present invention is illustrated and indicated generally at 60. The control circuit 60 is preferably mounted in the same housing as the power supply circuit 40 (see FIG. 10). The control circuit 60 uses a dual monostable multivibrator U1A and U1B (preferably a 4538) in order to generate two timing signals: the filament pre-heat signal and the exposure time signal. A short negative pulse to pin 11 of U1B causes pin 9 of U1B to switch from +12 V to ground for 1.0 second and then return to +12 V. The output signal on pin 9 of U1B is coupled through the diode D2 to the adjustable switching regulator U3 (preferably a LM1575adj, manufactured by National Semiconductor), as an enable signal. The switching regulator U3 produces an output voltage which is applied to output port 62 and is adjustable from +2 V to +11 V. The output port 62 is coupled to the center cap of the filament transformer T10 of FIG. 4.

Figure 4:
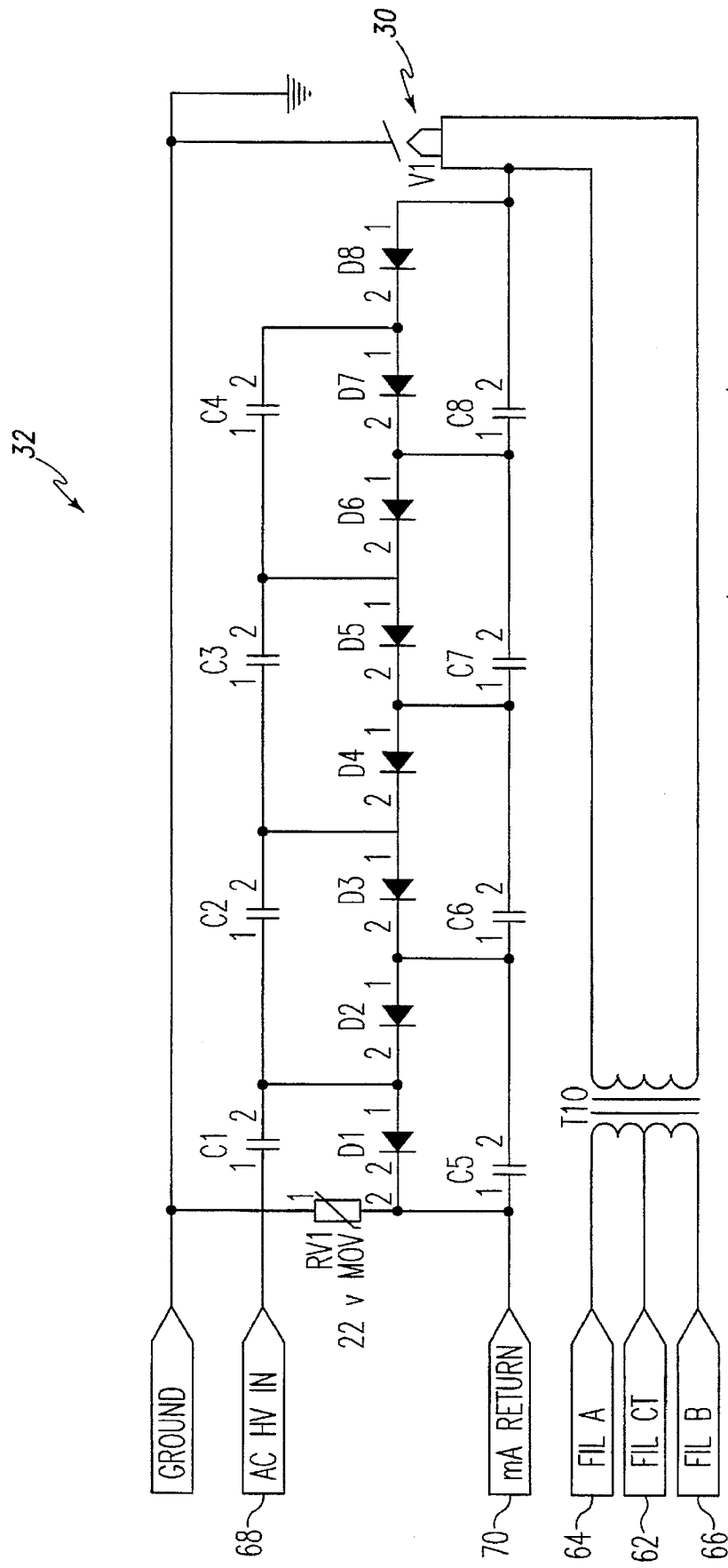
FIG. 4 is a schematic circuit diagram of an X-ray generator driving circuitry of the present invention.

The circuit of U4, Q3 and Q4 comprise a square wave power generator which is coupled to the filament transformer T10 of FIG. 4 via the output ports 64 and 66. Adjustment of the variable resistor R12 (coupled to U3) will set the filament voltage, and thus the X-ray generator tube 30 anode current. This filament current is on whenever U3 is enabled.

When the 1.0 second time interval ends, pin 10 of U1B feeds a signal to pin 5 of U1A in order to generate the exposure gate at pin 7 of U1A. The exposure gate signal feeds another diode D1 in order to enable U3 so that the filament circuit is energized for the sum of the pre-heat time (1.0 second) and the exposure time, whatever the exposure time may be. The exposure time is determined by the product of R1 and C1 at the input of U1A. A 0.1 second exposure time is indicated by the values of FIG. 3. However, R1 and C1 may be changed by a simple switching circuit so that variable exposure times can be selected by the operator. The resistance and capacitance values made available to the operator by such a switching circuit would be determined by the desired application for the X-ray generator. In a preferred embodiment, exposure times of 0.04, 0.06, 0.08, 0.10, 0.15, 0.20, 0.30, 0.40, 0.50 and 0.60 seconds are provided.

The exposure gate signal at pin 7 of U1A is also sent as an enable signal to U2 (preferably a SG3525), which is used as a low impedance square wave generator feeding two power FET's, Q1 and Q2. These two power FET's feed the high voltage transformer T11. The output of the high voltage transformer T11 is coupled to the output ports 68 and 70, which feed the voltage multiplier in the X-ray generator handle 12 (see FIGS. 1 and 4).

The circuit coupled to the ports 68 and 70 has a relatively large distributed capacitance which is coupled through the secondary of T11 to the primary of T11 as a relatively large capacitance. When the circuit switches from Q1 to Q2 or back to Q1, this capacitance makes the primary circuit of T11 look like a short circuit until that capacitance has been charged. A current limiting circuit of some type must therefore be used in order for the circuit to operate properly. In the present invention, the inductor L2 is used as a limiting inductor. When the capacitance is fully charged, the sudden change of current is limited by the inductor L2 and energy which is stored is released via the diode D4 into a small load resistor R18. If the X-ray generator tube 30 should happen to arc, higher voltage transients are limited by the diode D5 to the raw +160 VDC signal, which is sufficient to let transient signals dissipate their energy without damaging the FET's Q1 and Q2. Those skilled in the art will recognize that the circuit 60 relies on the insulation of transformer T11 and the insulation of filament transformer T10 (see FIG. 4) in order to prevent any connection between the user and the power line voltage.

A relaxation oscillator U20 (preferably a LM555) is also connected to the exposure gate signal provided by pin 7 of U1A. At the start of the gate, U20 will activate its output at pin 3 and energize a small beeper and an LED in order to indicate the exposure. The on time of U20 is approximately 0.5 seconds, enough to be seen and heard even when the actual exposure time is less than 0.01 seconds.

Federal safety rules and common sense require a "deadman" switch to be incorporated into the control circuitry for an X-ray generator. This means that the operator's exposure switch 38 will not permit X-ray emission from the X-ray generator tube 30 unless the dead-man enable switch 36 is also currently depressed. This is accomplished with a common relay 72 having contacts wired in series with the +100 VDC line. The enable switch 34 couples the +100 VDC voltage to the inductor L2 via the port 74.

Referring now to FIG. 4, the circuitry 32 located within the handle 12 of the portable X-ray generator is illustrated in greater detail. The high voltage circuit 32 operates at 25 kHz and incorporates a voltage 10-tupler. The filament circuit also operates at 25 kHz and the transformer T10 secondary comprises just three turns of insulated wire. The size and weight of the high voltage circuitry 32 are relatively low in order to allow the portable X-ray generator 10 of FIG. I to be easily handled by the operator. The filament transformer T10 utilizes a small ferrite core in order to further reduce the system weight.

Figure 5:
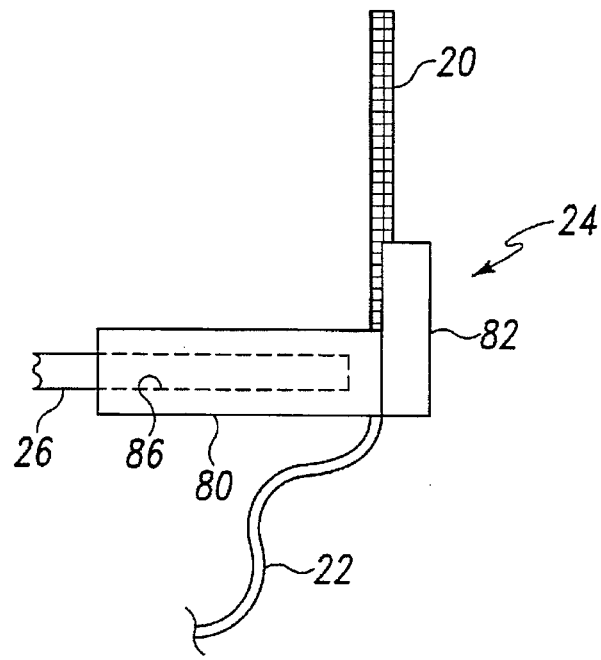
FIG. 5 is a side elevational view of a first embodiment receptor holder of the present invention.
Figures 6, 7:
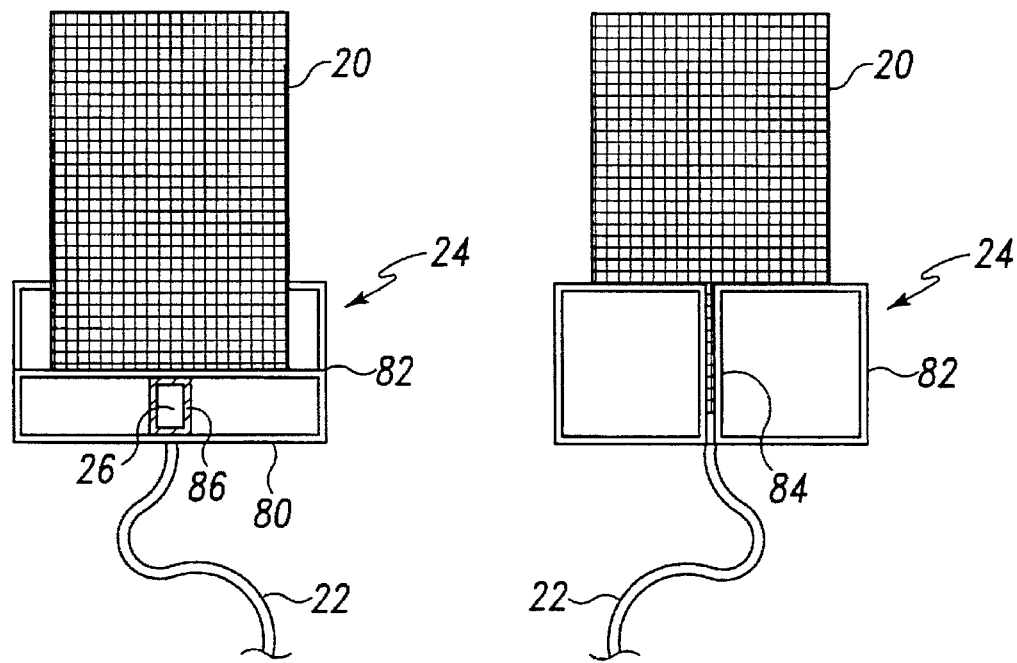
FIG. 6 is a first end elevational view of the receptor holder of FIG. 5.
FIG. 7 is a second end elevational view of the receptor holder of FIG. 5.

Referring now to FIGS. 5-7, a first embodiment of the X-ray receptor holder 24 is illustrated. The holder 24 comprises a horizontal portion 80 and an attached vertical portion 82. The X-ray receptor 20 fits securely within a recess formed at the junction between the members 80 and 82 as illustrated. A slot 84 is formed in the vertical member 82 in order to accommodate the wiring 22 which is used to control the X-ray receptor 20 and to download information therefrom when the receptor 20 is a CCD device. The horizontal member 80 includes a longitudinal slot 86 therein in order to mount the positioning bar 26 which engages the docking slots 28 of the X-ray tube 14. The use of the receptor holder 24 mounted to the positioning bar 26 will automatically create perfect parallelism between the sensor 20 and the portable X-ray generator 10, thus eliminating beam alignment problems due to erroneous vertical and horizontal angulations. In other words, the sensor 20 will always be perpendicular to the X-ray beam. This will reduce the patient's absorbed X-ray burden due to angulation errors, by eliminating retakes of poorly aligned receptors 20. Furthermore, the holder 24 and beam alignment arm 26 are detachable from the portable X-ray generator 10 and therefore may be autoclaved for later reuse.

Figure 8:
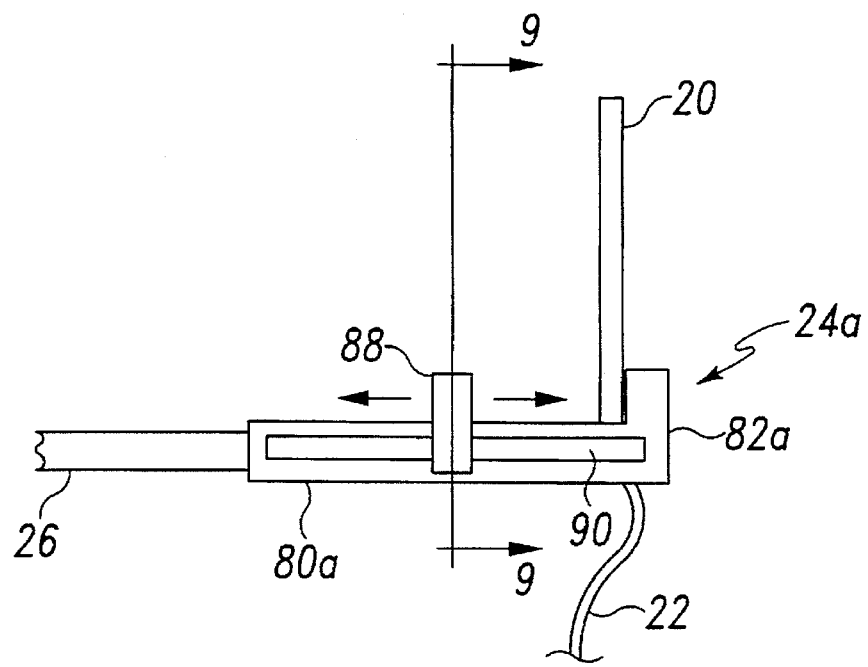
FIG. 8 is a side elevational view of a second embodiment receptor holder of the present invention.
Figure 9:
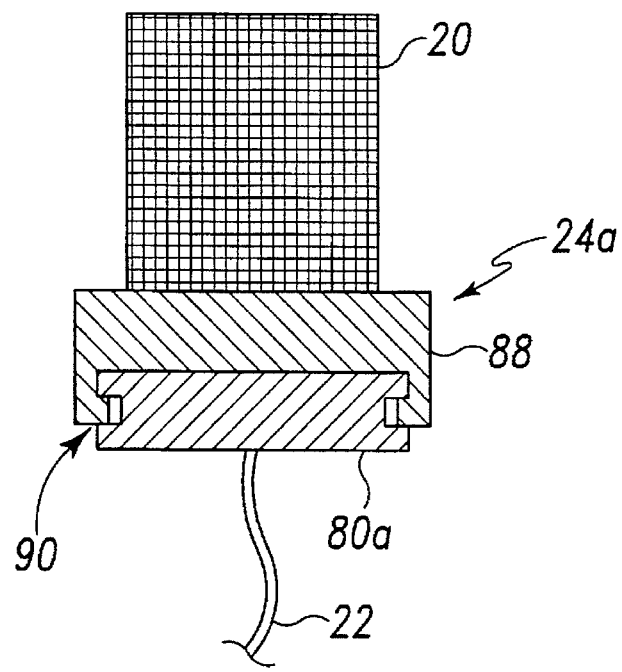
FIG. 9 is a cross-sectional view of the receptor holder of FIG. 8.

A second embodiment receptor holder is illustrated in FIGS. 8–9, and indicated generally at 24a. The holder 24a comprises a horizontal portion 80a and an attached vertical portion 82a. The horizontal member 80a includes a longitudinal slot (not shown) therein in order to mount the positioning bar 26 which engages the docking slots 28 of the X-ray tube 14. The X-ray receptor 20 may be placed at the junction between the members 80a and 82a as illustrated.

A slot (not shown) is formed in the vertical member 82a in order to accommodate the wiring 22 which is used to control the X-ray receptor 20 and to download information therefrom when the receptor 20 is a CCD device. The receptor 20 is held in place by means of a sliding box 88 which rides within the track 90 formed on either side of the horizontal member 80a. The sliding bar 88 allows the receptor holder 24 to be used with X-ray receptors 20 having any thickness. Because CCD receptors vary in thickness, and all are much thicker than X-ray film, the receptor holder 24a will accommodate any size receptor.

Figure 10:
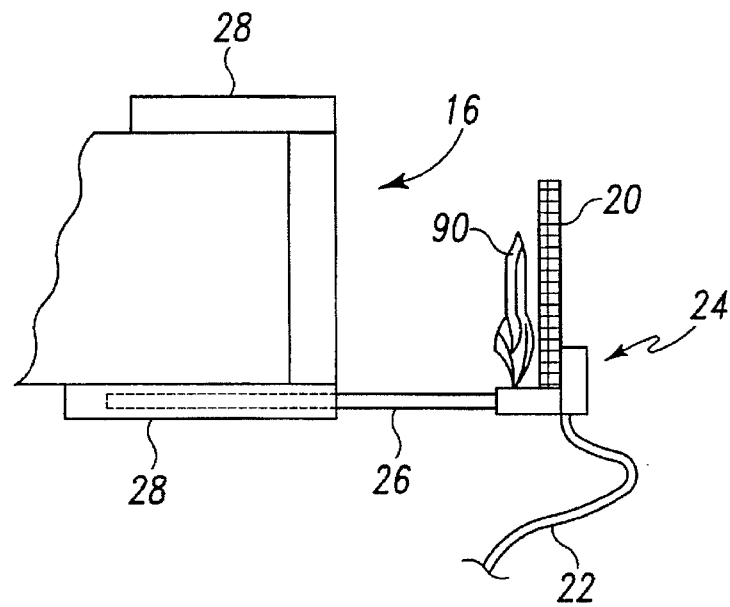
FIG. 10 is a side elevational view of the portable X-ray generator of the present invention making an X-ray image of a maxillary tooth.
Figure 11:
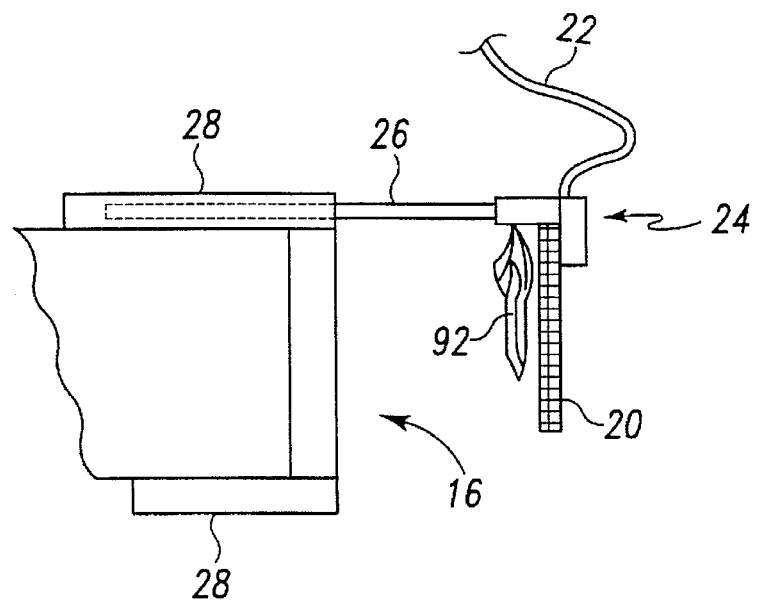
FIG. 11 is a side elevational view of the portable X-ray generator of the present invention making an X-ray image of a mandibular tooth.

Referring now to FIG. 10, use of the portable X-ray generator 10 in a dental application is illustrated, specifically with making an X-ray radiograph of a maxillary tooth 90. In this arrangement, the beam alignment arm 26 is placed in the lower docking slot 28 of the X-ray tube 14. This allows the receptor 20 and receptor holder 24 to be positioned within the patient's mouth and extend upwards behind the maxillary tooth 90. The corresponding positioning is shown in FIG. 11 for use of the portable X-ray device 10 with a mandibular tooth 92. In this orientation, the beam alignment arm is inserted into the upper docking slot 28 of the X-ray tube 14 so that the X-ray receptor 20 extends in a downward direction behind the mandibular tooth 92.

Figure 12:
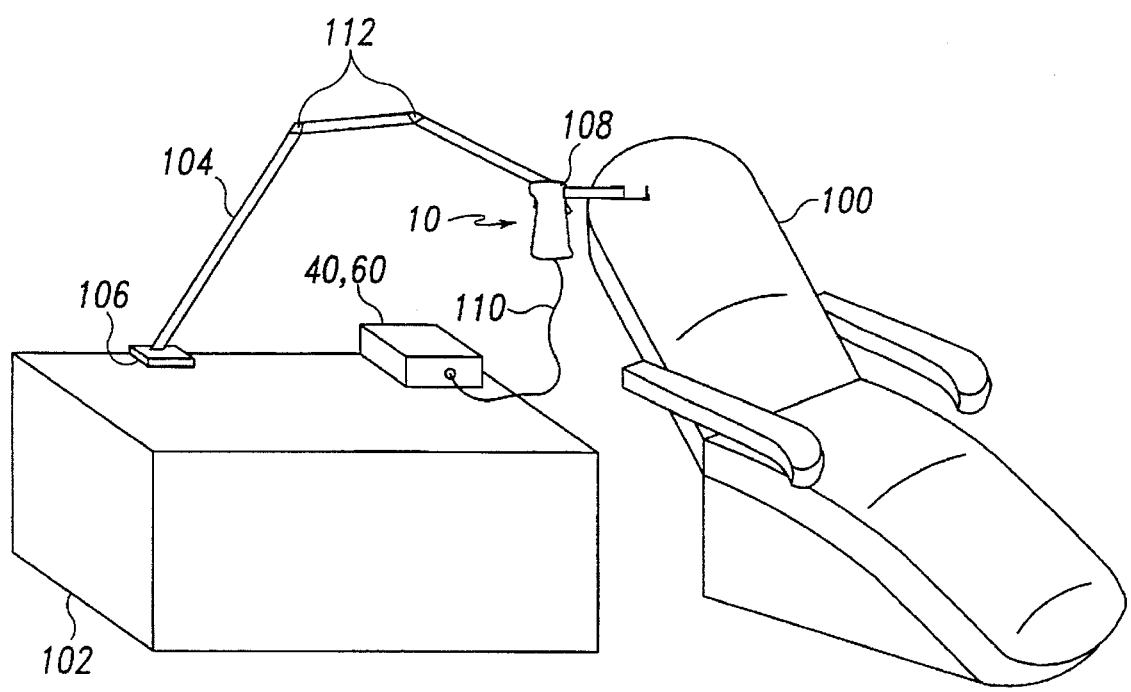
FIG. 12 is a perspective view of a dental operatory including the portable X-ray device of the present invention.

One of the advantages of the hand held X-ray device 10 of the present invention is that the hand held nature of the device allows not only ease of use by the X-ray technician, but also portability of the device from operatory to operatory. Such portability allows for a single hand-held X-ray unit 10 to be used in several different operatories, thereby greatly reducing the equipment and maintenance costs to the owner, such as a dentist, doctor, hospital, veterinarian, etc. Referring to FIG. 12, there is illustrated a first embodiment dental operatory which includes a portable X-ray device 10 of the present invention. A dental patient chair 100 is shown positioned next to a dental unit 102, which includes all of the tools and equipment needed by the dentist during a dental session. An articulating arm 104 is coupled to the dental unit 102 by means of a suitable connection 106. Alternatively, the articulating arm 104 may be freestanding and incorporate its own base (not shown). The distal end of the articulating arm 104 includes a cradle 108 which is adapted to releasably hold the portable X-ray unit 10. The power supply and control circuits 40, 60 of the X-ray unit are housed in an appropriate box which may be placed on or within the dental unit 102. A cable 110 couples the portable X-ray unit 10 to these circuits. The articulating arm 104 has a plurality of movable joints 112 which allow for adjustable positioning of the portable X-ray unit 10 in relation to the patient. A collection of operatories which share a portable X-ray unit 10 may be configured in several different ways. For example, each operatory may include its own articulating arm 104 and control circuitry 40, 60, while a single portable X-ray unit 10 and cable 110 is transported from operatory to operatory. The provision of the cradle 108 on the end of the articulating arm 104 provides for quick and convenient connection of the portable X-ray unit 10 into the equipment of the operatory. Alternatively, each operatory may be equipped with an articulating arm 104 and the control circuitry 40, 60 and portable X-ray generator 10 may be transported from operatory to operatory as a unit. This would further reduce the equipment costs experienced by the owner.

If an articulating arm 104 is utilized to hold the portable X-ray unit 10 during operation, a remote control firing mechanism may be used in place of the enable and fire switches 36 and 38 on the unit 10. Such remote control firing mechanism may be hard wired to the unit 10, or may be a wireless remote control utilizing infrared or low frequency RF signals. The use of such a remote control firing mechanism will allow the operator to leave the room prior to the generation of X-rays by the portable X-ray generator 10. Alternatively, the portable X-ray generator 10 may be utilized by the operator without leaving the room due to the greatly reduced X-ray dose which is generated by the X-ray generator 10. In this situation, the use of the articulating arm 104 will be optional, as the operator may simply hold the X-ray generator 10 in his or her hand during use. A further option is that the cable 110 may be integrated into the articulating arm 104 and terminate at a connector (not shown) within the cradle 108, such that the portable X-ray generator 10 may be coupled to the cradle 108 wherein the connector 34 of the portable X-ray generator 10 mates with the connector on the end of the cable 110. Such an arrangement will minimize the number of wires which are exposed at the dental unit 102.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A portable X-ray device, comprising:
   a handle configured to be held by a single hand;
   an X-ray tube mounted within the handle;
   a collimated tube mounted to the handle and positioned such that X-rays will be emitted into the collimated tube when the X-ray tube is activated;
   wiring extending between an interior of the handle and an exterior of the handle and operative to couple an external power supply to the X-ray tube;
   an enable switch mounted to the handle; and
   an exposure switch mounted to the handle;
   wherein the X-ray tube will only emit X-rays when the enable switch and the exposure switch are both depressed.

2. The portable X-ray device of claim 1, further comprising:
   power supply circuitry operative to generate a voltage to drive the X-ray tube; and
   control circuitry operative to control an exposure time of the X-ray tube;
   wherein the power supply circuitry and the control circuitry are not contained within the handle and are coupled to the handle by the wiring;
   whereby a weight of the handle is significantly reduced.

3. The portable X-ray device of claim 2, wherein the control circuitry causes a warm-up current to be applied to the X-ray tube when the enable switch is depressed.

4. The portable X-ray device of claim 2, wherein the control circuitry causes the power supply circuitry to generate the drive voltage when the exposure switch is depressed.

5. The portable X-ray device of claim 1, further comprising:
   a multi-pin connector coupled to the handle and conductively coupled to the wiring.

6. The portable X-ray device of claim 1, further comprising:
   an image receptor holder coupled to the collimated tube, the holder comprising:
   a horizontal member having proximal and distal ends;
   a vertical member attached to the horizontal member distal end and extending transversely thereto; and
   a transverse sliding member mounted to the horizontal member and operative to slide thereon in a longitudinal direction;
   wherein an X-ray image receptor may be held between the vertical member and the sliding member.

7. The portable X-ray device of claim 6, wherein the X-ray image receptor is a CCD array.

8. The portable X-ray device of claim 1, further comprising:
   a cradle adapted to hold the X-ray device when placed therein, wherein a position of the cradle with respect to a patient is adjustable.

9. A portable X-ray device, comprising:
   an enclosure;
   an X-ray tube mounted within the enclosure;
   a collimated tube mounted to the enclosure and positioned such that X-rays will be emitted into the collimated tube when the X-ray tube is activated;
   wiring extending between an interior of the enclosure and an exterior of the enclosure and operative to couple an external power supply to the X-ray tube;
   power supply circuitry operative to generate a voltage to drive the X-ray tube, wherein the power supply circuitry is not contained within the enclosure and is coupled to the enclosure by the wiring;
   whereby a weight of the enclosure is significantly reduced;
   control circuitry operative to control an exposure time of the X-ray tube, wherein the control circuitry is not contained within the enclosure and is coupled to the enclosure by the wiring;
   a remote control receiver coupled to the power supply and control circuitry; and
   a remote control transmitter operable for wireless transmission of an enable signal and an exposure signal to the remote control receiver;
   wherein the control circuitry causes a warm-up current to be applied to the X-ray tube when the enable signal is received by the remote control receiver.

10. The portable X-ray device of claim 9, further comprising:
    a cradle adapted to hold the X-ray device when placed therein, wherein a position of the cradle with respect to a patient is adjustable.

11. The portable X-ray device of claim 9, further comprising:
    an image receptor holder coupled to the collimated tube, the holder comprising:
    a horizontal member having proximal and distal ends;

a vertical member attached to the horizontal member distal end and extending transversely thereto; and a transverse sliding member mounted to the horizontal member and operative to slide thereon in a longitudinal direction;

wherein an X-ray image receptor may be held between the vertical member and the sliding member.

12. The portable X-ray device of claim 11, wherein the X-ray image receptor is a CCD array.

13. The portable X-ray device of claim 9, wherein the control circuitry causes the power supply circuitry to generate the drive voltage when the exposure signal is received by the remote control receiver.

14. The portable X-ray device of claim 9, further comprising:

a multi-pin connector coupled to the enclosure and conductively coupled to the wiring.

15. A method for generating an X-ray image, comprising the steps of:

(a) providing a portable X-ray device, comprising:
a handle configured to be held by a single hand;
an X-ray tube mounted within the handle;
a collimated tube mounted to the handle and positioned such that X-rays will be emitted into the collimated tube when the X-ray tube is activated;
wiring extending between an interior of the handle and an exterior of the handle and operative to couple an external power supply to the X-ray tube;
an enable switch mounted to the handle; and
an exposure switch mounted to the handle;
wherein the X-ray tube will only emit X-rays when the enable switch and the exposure switch are both depressed.

(b) grasping the handle with a single hand;

(c) depressing the enable switch with a first finger of the hand;

(d) aiming the collimated tube at an X-ray image receptor, wherein a structure to be imaged is positioned between the collimated tube and the receptor; and (e) depressing the exposure switch with a second finger of the hand while holding the enable switch in a depressed position.

16. A method for generating an X-ray image, comprising the step of:

(a) providing a portable X-ray device, comprising:
an enclosure;
an X-ray tube mounted within the enclosure;
a collimated tube mounted to the enclosure and positioned such that X-rays will be emitted into the collimated tube when the X-ray tube is activated;
wiring extending between an interior of the enclosure and an exterior of the enclosure and operative to couple an external power supply to the X-ray tube; and
power supply circuitry operative to generate a voltage to drive the X-ray tube, wherein the power supply circuitry is not contained within the enclosure and is coupled to the enclosure by the wiring;
whereby a weight of the enclosure is significantly reduced;

(b) providing an articulating arm having a cradle thereon, wherein the cradle is adapted to hold the X-ray device when placed therein;

(c) aiming the collimated tube at an X-ray image receptor, wherein a structure to be imaged is positioned between the collimated tube and the receptor;

(d) moving the articulated arm such that the cradle will hold the X-ray device;

(e) depressing an enable switch; and (f) depressing an exposure switch, wherein the X-ray device will not emit X-rays unless both the enable switch and the exposure switch are depressed.

17. The method of claim 16, wherein the enable switch and the exposure switch are coupled to the X-ray device by wireless remote control.

* * * * *